United States Patent
Sasaki et al.

(12)

(10) Patent No.: US 6,411,672 B1
(45) Date of Patent: Jun. 25, 2002

(54) RADIATION DETECTOR AND X-RAY CT APPARATUS

(75) Inventors: Tomiya Sasaki; Sakae Kimishima, both of Nasu-gun (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/595,545

(22) Filed: Jun. 16, 2000

(30) Foreign Application Priority Data

Jun. 18, 1999 (JP) .......................................... 11-173023

(51) Int. Cl.$^7$ ................................................. A61B 6/03
(52) U.S. Cl. ..................................... 378/19; 250/370.15
(58) Field of Search ........................... 378/19, 141, 142, 378/98.8; 250/370.15

(56) References Cited

U.S. PATENT DOCUMENTS 6,052,429 A * 4/2000 Ohno et al. .................... 378/45

FOREIGN PATENT DOCUMENTS

| JP | 62-003684 | 1/1987 |
|---|---|---|
| JP | 3-258248 | 11/1991 |
| JP | 2001-057974 | * 3/2001 |

* cited by examiner

*Primary Examiner*—Drew Dunn
(74) *Attorney, Agent, or Firm*—Oblon, Spivak, McClelland, Maier & Neustadt, P.C.

(57) ABSTRACT

An X-ray CT radiation detector includes a heat insulating case mounted on a rotating base, a radiation incident window formed in the heat insulating case, a detection panel on which detection elements for detecting radiation incident through the radiation incident window are arrayed. The detection panel is positioned to form a fluid circulatory path in the heat insulating case. A circulator for circulating the fluid is placed in the circulatory path. The circulatory path and circulation of the fluid by the circulator make it possible to make the temperature of the detection panel relatively uniform.

19 Claims, 2 Drawing Sheets

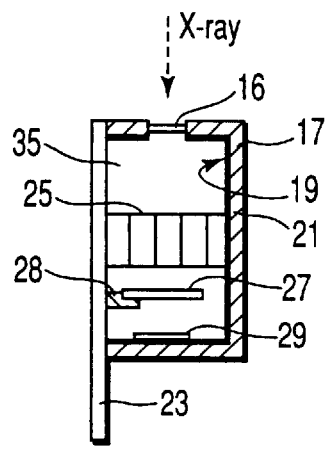
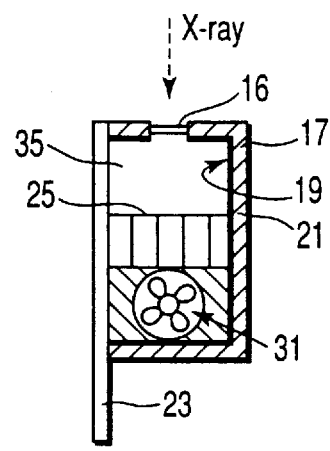
FIG. 3A          FIG. 3B
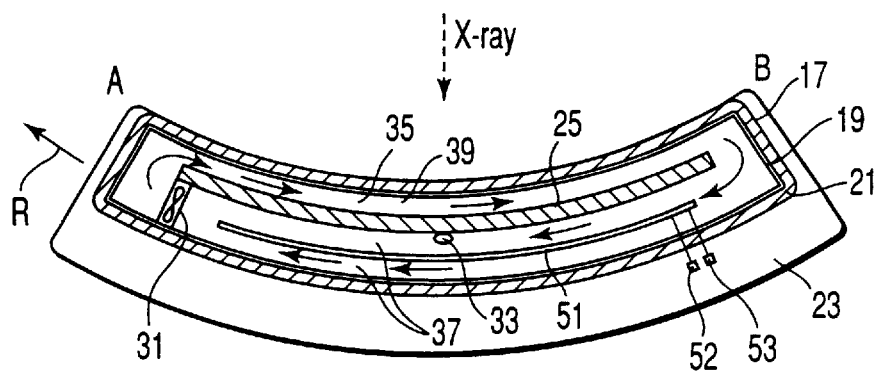
FIG. 4
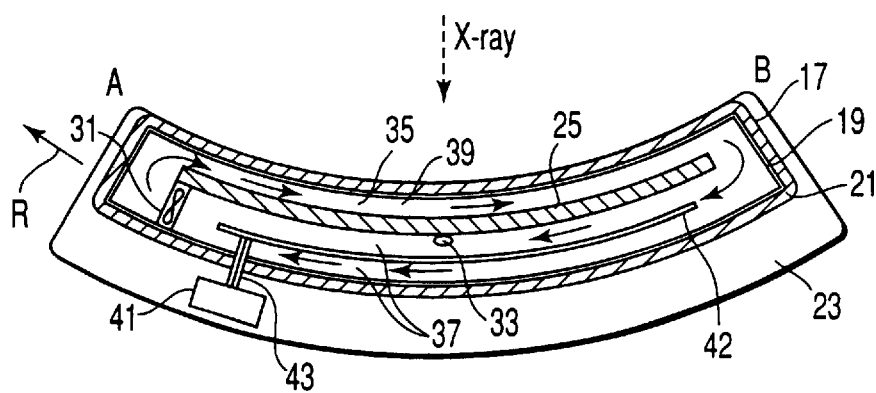
FIG. 5

RADIATION DETECTOR AND X-RAY CT APPARATUS

CROSS-REFERENCE TO RELATED APPLICATIONS

This application is based upon and claims the benefit of priority from the prior Japanese Patent Application No. 11-173023, filed Jun. 18, 1999, the entire contents of which are incorporated herein by reference.

BACKGROUND OF THE INVENTION

The present invention relates to a radiation detector mounted in an X-ray CT (Computed Tomography) apparatus having the function of acquiring multidirectional projection data and the function of reconstructing a tomographic image based on the acquired data, and the X-ray CT apparatus.

Recently, as an X-ray CT radiation detector, a detector using solid-state detection elements using scintillators or X-ray detection elements has been developed. According to the detection principle of this device, as is known, the energy that X-rays lose due to ionization in a depletion layer formed upon application of a reverse bias to the rectifier junction of a diode is extracted as a current. Since energy conversion from X-rays to electric charges is direct and efficient, the energy resolution is very high, and the spatial resolution is also high. For this reason, this device is expected to be used widely in the future. In general, a one- or two-dimensional array of these solid-state detection elements is mounted on the rotating base of a gantry while being housed in an optically sealed case.

This solid-state detection element generally has temperature dependence, so that a temperature environment in which the device exhibits most efficient conversion efficiency is produced by using a heat panel. More specifically, a heat panel is mounted on the outside of the case to heat the overall case by using high thermal conductivity of the case consisting of aluminum or the like.

In general, several thousand channels are prepared for the X-ray CT radiation detector. If one solid-state detection element is used for one channel, several thousand solid-state detection elements are required. In this case, a problem arises in terms of temperature nonuniformity. Even if temperature dependence is made uniform among solid-state detection elements, variations in environmental temperature for each element will produce errors in output signals, resulting in artifacts (false images). The problem of temperature nonuniformity becomes increasingly significant owing to a high cooling effect produced as the gantry rotates at high speed for the purpose of shortening the scan time.

More specifically, a solid-state detection element array and collimator are mounted in an optically sealed cast case, and the temperature in the case is kept constant by using a heat panel stuck on the outer surface of the case and temperature control. From the viewpoint of the flow of heat, the heat generated by the heat panel is transferred to the overall case and base and spreads to the overall radiation detector. During the rotation of the gantry, however, the temperature of the head portion of the case, in particular, extremely drops due to a cooling effect. On the other hand, if the heat value of the heat panel is increased to suppress the cooling of the head portion, the portion other than the head portion is excessively heated. Currently, attempts to solve this problem have been repeatedly made on a trial-and-error basis in the process of selecting materials for a case and designing its shape. However, no satisfactory results have been obtained. In addition, this method undesirably limits the degree of freedom in case design, and hence cannot flexibly cope with changes in size, weight, cost, and the like.

BRIEF SUMMARY OF THE INVENTION

It is an object of the present invention to provide a radiation detector and X-ray CT apparatus which can make internal temperature more uniform with a relatively simple structure.

A radiation detector for X-ray CT includes a heat insulating case mounted on a rotating base, a radiation incident window formed in the heat insulating case, a detection panel on which detection elements for detecting radiation incident through the radiation incident window are arrayed. The detection panel is positioned to form a fluid circulatory path in the heat insulating case. A circulator for circulating the fluid is placed in the circulatory path. The circulatory path and circulation of the fluid by the circulator make it possible to make the temperature of the detection panel relatively uniform.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3A is a cross-sectional view taken along a line a—a in FIG. 2;

FIG. 3B is a cross-sectional view taken along a line b—b in FIG. 2;

FIG. 4 is a longitudinal sectional view of an X-ray CT radiation detector according to the second embodiment of the present invention; and FIG. 5 is a longitudinal sectional view of an X-ray CT radiation detector according to the third embodiment of the present invention.

DETAILED DESCRIPTION OF THE INVENTION

Radiation detectors according to preferred embodiments of the present invention will be described in detail below with reference to the views of the accompanying drawing. Assume that a radiation detector is mounted in an X-ray computed tomography (X-ray CT) apparatus. The radiation detector according to the present invention, however, can be mounted in any apparatus that has the function of detecting radiation other than X-ray CT apparatus. As is known, an X-ray CT apparatus includes a gantry and computer system. The gantry has a ring-like rotating base, an X-ray tube mounted on the rotating base, and a radiation detector mounted on the rotating base. The computer system has a processor for generating an image (tomographic image) on the basis of an output from the radiation detector.

(First Embodiment)

Figure 1:
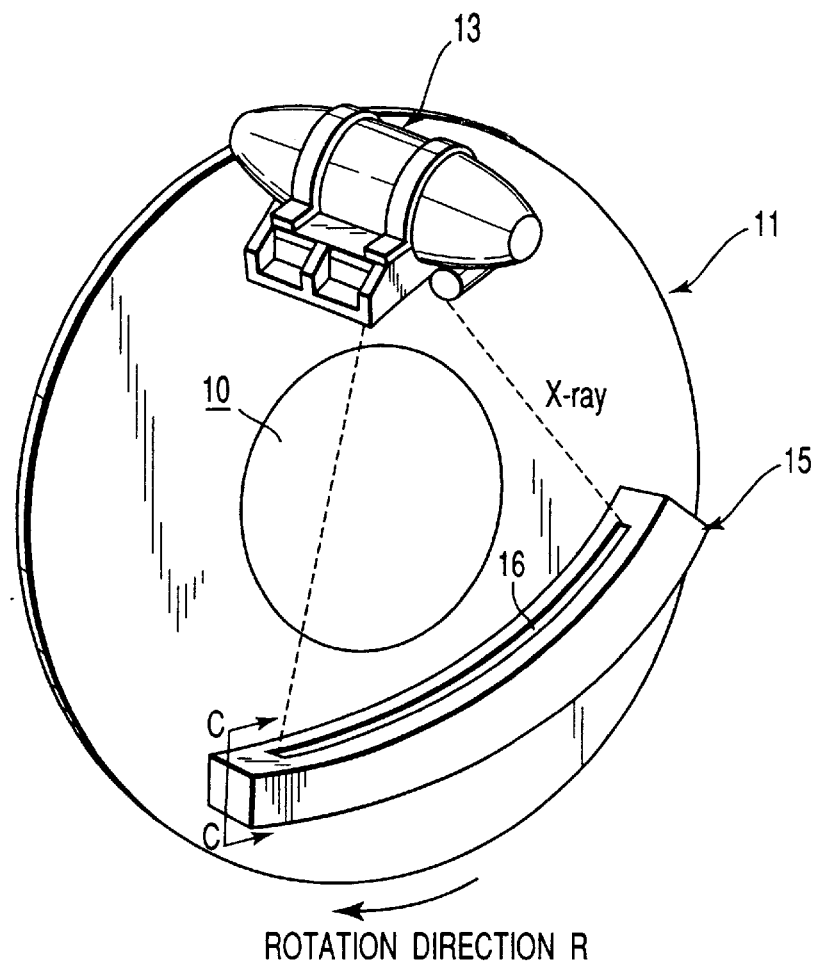
FIG. 1 is a perspective view showing a mounted state of an X-ray CT radiation detector according to the first embodiment of the present invention.

As shown in FIG. 1, an X-ray tube 13 for generating X-rays (radiation) in the form of a fan is mounted on a ring-like rotating base 11. A radiation detector 15 is mounted on the rotating base 11. An X-ray incident window 16 of the radiation detector 15 faces the X-ray tube 13. The radiation detector 15 can therefore detect X-rays transmitted through an object placed in a photographing area 10. The X-rays generated by the X-ray tube 13, transmitted through the object, and collimated by a collimator enter the radiation detector 15 through the X-ray incident window 16.

The radiation detector 15 generates a signal current having a peak value corresponding to the intensity of incident X-rays. This signal current is amplified and converted into a digital signal in a circuit box (not shown). This signal is held in a memory in correspondence with a channel code and angle code. Tomographic image data is reconstructed by a computer on the basis of projection data corresponding to one rotation (360°) or 180°+α(α is the fan angle) prepared by repeating this operation during the rotation of the rotating base 11.

Figure 2:
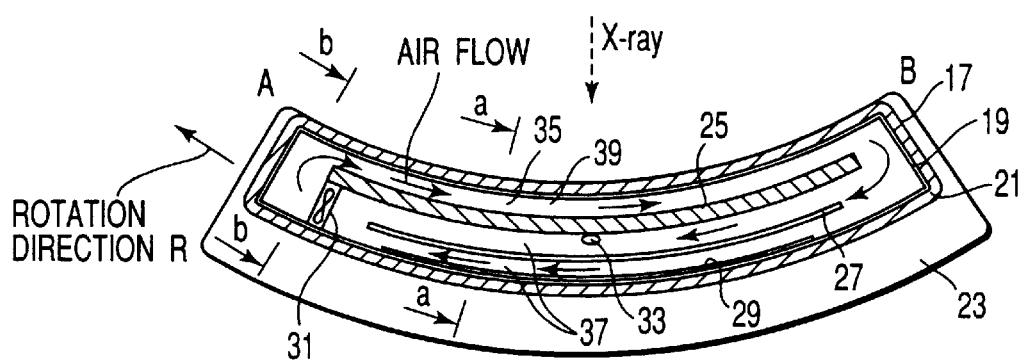
FIG. 2 is a longitudinal sectional view taken along a line c—c in FIG. 1.

FIG. 2 is a longitudinal sectional view taken along a line c—c in FIG. 1; FIG. 3A, a cross-sectional view taken along a line a—a in FIG. 2; and FIG. 3B, a cross-sectional view taken along a line b—b in FIG. 3B. An optically sealed arcuated internal space is provided by a plate-like base 23 and case 17 having a substantially C-shaped cross section. A solid-state detection element array 25 formed on a substrate is housed in this space. The solid-state detection element array 25 is made up of a plurality of solid-state detection elements for directly converting X-rays into a signal current. The plurality of solid-state detection elements are arrayed in a line in the direction in which X-rays diverge. The plurality of solid-state detection elements may be arranged in the form of a matrix.

The case 17 is comprised of a housing 19 made of a high-terminal-conductivity metal such as iron and a heat insulator 21 covering the outer surface of the housing 19. This structure contributes to uniform internal temperature with high thermal conductivity inside the case as in the prior art, and realizes a high heat insulating effect and high heat retaining effect with respect to the outside of the case. In consideration of thermal conductivity, the housing 19 preferably has a thickness of 1 mm or more.

As shown in FIGS. 3A and 3B, the solid-state detection element array 25 is placed at an almost middle position in the internal space in the form of a bridge between a surface of the base 23 and the internal surface of the case 17. With this structure, the internal space is partitioned by the solid-state detection element array 25 into a space 35 located on the upper surface side and elongated along a rotation direction R and a space 37 located on the lower surface side and elongated along the rotation direction R. Gaps are ensured between the two ends of the solid-state detection element array 25 and the inner surfaces of the two ends of the case 17. The space 35 on the upper surface side communicates with the space 37 on the lower surface side through these gaps. With this structure, a circulatory flow path 39 for internal air, which is elongated along the rotation direction R, is formed in the internal space.

A main heat panel 27 which is stuck to an aluminum plate and used to heat internal air is placed, while being cantilevered from the base 23, in the lower-surface-side space 37 in the circulatory flow path 39 which exerts little influence on X-ray detection. More specifically, the main heat panel 27 is placed at an almost middle position in the lower-surface-side space 37 in a suspended state therein to be slightly separated from both the solid-state detection element array 25 at an upper position and the bottom surface of the case 17 at a lower position so as to ensure small upper and lower spaces. A sub-heat panel 29 serving as an auxiliary unit for the main heat panel 27 is stuck on the upper surface of the housing 19 of the case 17 in the lower-surface-side space 37 which exerts little influence on X-ray detection.

In the circulatory flow path 39, a compact fan 31 for forcibly circulating internal air is placed on the lower surface side which exerts little influence on X-ray detection. Since the fan 31 circulates internal air, the uniformity of internal temperature can be improved.

This fan 31 is placed at an effective mounting position where heated air directly collides against a head portion A of the case 17 which is subjected most to a cooling effect produced by the rotation of the radiation detector 15. The heat panels 27 and 29 are positioned for this purpose. Positioning the fan 31 in this manner maximizes the heating effect at the head portion A of the case 17, which is subjected most to the cooling effect produced by the rotation of the X-ray CT radiation detector 15, thus effectively making the internal temperature uniform.

A temperature sensor 33 is mounted at an almost middle position in the circulatory flow path 39 which is located on the lower surface side that has little influence on X-ray detection and allows relatively easy measurement of an average internal temperature. The heat values of the heat panels 27 and 29 and the quantity of air supplied by the fan 31 are controlled by a controller (not shown) in accordance with an output from the temperature sensor 33, thereby keeping the internal temperature almost constant.

As is obvious from the flow of heat in the radiation detector 15 of this embodiment having the above arrangement, the heat generated by heat panel 27 is forcibly circulated, together with internal air, along the circulatory flow path 39 by the fan 31. Covering the overall radiation detector 15 with the heat insulator 21 makes it difficult for heat to escape outside the radiation detector 15, thereby protecting it against an external cooling effect. In addition, heat is transferred throughout the overall radiation detector 15 via the metal housing 17 by the sub-heat panel 29. This effect makes the temperature of the radiation detector 15 further uniform.

When the rotating base 11 rotates, the head portion A of the radiation detector 15 is especially cooled in the rotation direction R. As in this embodiment, the temperature of the radiation detector 15 is made uniform by forcibly circulating the internal air in the radiation detector 15 using the fan 31. In addition, the internal air directly collides against the head portion A by the fan 31 immediately after the air is heated by the heat panels 27 and 29, i.e., while the air is set at the highest temperature. This further improves the effect of making temperature uniform. In addition, attaching the base 23 to a gantry body makes it easy for heat to escape owing to thermal conduction (as in the prior art). However, since hot air is circulated as described above, temperature control can be performed with a minimum change in temperature unlike the prior art in which control is performed only by thermal conduction.

As described above, according to this embodiment, since internal air is forcibly circulated along the circulatory flow path by the fan, uniformity of internal temperature improves. In addition, since temperature control does not depend on only the thermal conduction of the case, case design is facilitated. At the same time, reductions in the weight and cost of the case can be expected.

(Second Embodiment)

When different metals are joined to each other, and a current is supplied to the joint surface, heat is generated or absorbed. The amount of heat generated or absorbed can be adjusted by adjusting the current to be supplied. In addition, generation and absorption of heat can be switched by changing the direction of a current. This phenomenon is known as the Peltier effect.

In this embodiment, in place of the heat panel 27, a Peltier device 51 having the Peltier effect and worked into a panel-like shape is housed in a case 17. Two electrodes 52 and 53 are extracted from the Peltier device 51 to the outside of the case 17 through leads.

The degrees of heating or cooling and switching between heating and cooling can be controlled by the currents supplied to the electrodes 52 and 53 and their directions.

According to this embodiment, in addition to the effects of the first embodiment, cooling can be performed as well as heating, and internal temperature can be finely controlled.

(Third Embodiment)

In this embodiment, in place of the Peltier device 51 in the second embodiment, a heat exchanger 42 in the form of a panel is placed in a case 17, and heating or heat absorption is realized by a heat exchange system. This heat exchanger 42 is joined to another heat exchanger 41 mounted on a base 23 through a pipe 43 to form a circulatory path for an arbitrary type of coolant. Note that the position of the heat exchanger 41 is not limited to a position near the solid-state detection element array 25, and the heat exchanger 41 can be mounted at any position, e.g., a position near the X-ray tube, as long as it is mounted on the rotating base 11. Although not shown, a compressor and four-way valve are placed midway along this circulatory path. By reversing the flow of the coolant using the four-way valve, the heating function and heat absorbing function of the heat exchanger 42 can be switched. In addition, the degree of heating or cooling can be controlled by adjusting the compression ratio of the compressor.

According to this embodiment, like the second embodiment, internal temperature can be finely controlled.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT apparatus comprising:
   a rotating base;
   an X-ray tube mounted on said rotating base;
   a radiation detector mounted on said rotating base to oppose said X-ray tube through a photographing area; and
   a processor for generating an image on the basis of an output from said radiation detector,
   wherein said radiation detector comprises:
   a heat insulating case mounted on said rotating base;
   a radiation incident window formed in said heat insulting case,
   a detection panel on which detection elements for detecting radiation incident through said radiation incident window are arrayed;
   a fluid circulatory path formed in said heat insulating case by said detection panel; and
   a circulator for circulating a fluid in said circulatory path.

2. An apparatus according to claim 1, wherein said radiation detector further comprises at least one heater placed in said circulatory path.

3. An apparatus according to claim 2, wherein said radiation detector further comprises at least one sub-heater placed in said circulatory path.

4. An apparatus according to claim 1, wherein said radiation detector further comprises at least one heating/heat absorbing panel having the Peltier effect and placed in said circulatory path.

5. An apparatus according to claim 1, wherein said radiation detector further comprises at least one heat exchanger placed in said circulatory path.

6. An apparatus according to claim 1, wherein an interior of said heat insulating case is partitioned by said detection panel into an elongated space on a side of said radiation incident window and an elongated space on a side opposite to said radiation incident window, and the two spaces are jointed to each other at two ends to form said circulatory path.

7. An apparatus according to claim 1, wherein said circulator is a fan.

8. An apparatus according to claim 1, wherein said circulator is placed near a head portion of said heat insulating case during rotation of said rotating base.

9. An apparatus according to claim 1, wherein said circulator is placed near one end of said detection panel.

10. An apparatus according to claim 1, wherein said heat insulating case comprises a metal case having a relatively high thermal conductivity and a heat insulating member covering an outer surface of said metal case.

11. An apparatus according to claim 10, wherein at least one heater panel and at least one heating/heat absorbing panel having the Peltier effect or at least one heat exchanger are arranged in contact with each other on an inner surface of said metal case.

12. An apparatus according to claim 1, wherein said radiation detector further comprises a plurality of heat exchangers, and at least one of said plurality of heat exchangers is disposed in contact with an inner surface of said metal case.

13. An apparatus according to claim 1, wherein said radiation detector further comprises at least one temperature sensor placed midway along said circulatory path.

14. An X-ray CT apparatus comprising:
   a rotating base;
   an X-ray tube mounted on said rotating base;
   a radiation detector mounted on said rotating base to oppose said X-ray tube through a photographing area; and
   a processor for generating an image on the basis of an output from said radiation detector,
   wherein said radiation detector comprises:
   a detection panel on which detection elements for detecting radiation emitted from said X-ray tube and passed through a subject are arrayed
   a container mounted on said rotating base to contain said detection panel; and
   a fluid circulatory path formed in said container by said detection panel.

15. An X-ray CT apparatus comprising:
   a rotating base;

an X-ray tube mounted on said rotating base;

a radiation detector mounted on said rotating base to oppose said X-ray tube through a photographing area; and a processor for generating an image on the basis of an output from said radiation detector, wherein said radiation detector comprises:

a heat insulating case mounted on said rotating base;

a radiation incident window formed in said heat insulating case;

a detection panel on which detection elements or detecting a radiation incident through said radiation incident window are arrayed, said detection panel being housed in said heat insulating case; and at least one heating/heat absorbing panel having the Peltier effect or at least one heat exchanger, said heating/heat absorbing panel or said heat exchanger being housed in said heat insulating case.

16. A radiation detector comprising:

a heat insulating case mounted on a base;

a radiation incident window formed in said heat insulating case;

a detection panel on which detection elements for detecting a radiation incident through said radiation incident window are arrayed;

a fluid circulatory path formed in said heat insulating case by said detection panel; and a circulator for circulating a fluid in said circulatory path.

17. A radiation detector comprising:

a heat insulating case;

a radiation incident window formed in said case;

a detection panel on which detection elements for detecting radiation incident through said radiation incident window are arrayed; and a fluid circulatory path formed in said case.

18. An apparatus according to claim 14, wherein said radiation detector further comprises a circulator to circulate a fluid in said circulatory path.

19. An apparatus according to claim 14, wherein said container comprises a plate-like base and case having a substantially C-shaped cross section.

* * * * *